United States Patent
Ragil et al.

(10) Patent No.: US 6,353,144 B1
(45) Date of Patent: Mar. 5, 2002

(54) PROCESS FOR CHROMATOGRAPHIC SEPARATION OF A C5-C8 FEED OR AN INTERMEDIATE FEED INTO THREE EFFLUENTS, RESPECTIVELY RICH IN STRAIGHT CHAIN, MONO-BRANCHED AND MULTI-BRANCHED PARAFFINS

(75) Inventors: Karine Ragil, Rueil Malmaison; Michel Bailly, Nancy; Sophie Jullian, Rueil Malmaison; Olivier Clause, Chatour, all of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/244,428

(22) Filed: Feb. 4, 1999

(30) Foreign Application Priority Data

Feb. 4, 1998 (FR) ............................. 98/01390

(51) Int. Cl.$^7$ .............................. C07C 7/12; C07C 5/13; C10G 25/00; C10G 7/02
(52) U.S. Cl. .................. 585/825; 585/803; 585/820; 585/822; 585/826; 585/737; 585/738; 208/351; 208/310 R; 208/310 Z
(58) Field of Search ................ 585/803, 825, 585/820, 822, 826, 737, 738; 208/351, 310 R, 310 Z

(56) References Cited

U.S. PATENT DOCUMENTS

| | | | |
|---|---|---|---|
| 4,426,292 A | 1/1984 | Wernick et al. | 210/635 |
| 4,855,529 A * | 8/1989 | Stem et al. | 585/737 |
| 4,982,048 A * | 1/1991 | Stem et al. | 585/751 |
| 5,055,633 A * | 10/1991 | Volles | 585/826 |
| 5,055,634 A | 10/1991 | Volles | 585/826 |
| 5,107,052 A | 4/1992 | McCulloch et al. | 585/738 |
| 5,530,172 A * | 6/1996 | Funk et al. | 585/736 |

FOREIGN PATENT DOCUMENTS

| FR | 2 496 486 | 6/1982 |
|---|---|---|
| FR | 2 276 867 | 1/1996 |

* cited by examiner

*Primary Examiner*—Walter D. Griffin
*Assistant Examiner*—Tam M. Nguyen
(74) *Attorney, Agent, or Firm*—Millen, White, Zelano & Branigan, P.C.

(57) ABSTRACT

For producing three effluents which are respectively rich in straight chain paraffins, in mono-branched paraffins, and in di-branched and tri-branched paraffins possibly with naphthenic and/or aromatic compounds, from C5–C8 cuts or intermediate cuts (C5–C7, C6–C8, C7–C8, C6–C7, C7 or C8), comprising paraffinic and possibly naphthenic and/or aromatic hydrocarbons, and in some cases olefinic hydrocarbons, a chromatographic separation process uses a separation zone operating by adsorption. The process of the invention is of particular application when coupled with a hydro-isomerization process, which selectively recycles straight chain and mono-branched paraffins, necessary for paraffins containing at least 7 carbon atoms.

27 Claims, No Drawings

PROCESS FOR CHROMATOGRAPHIC SEPARATION OF A C5-C8 FEED OR AN INTERMEDIATE FEED INTO THREE EFFLUENTS, RESPECTIVELY RICH IN STRAIGHT CHAIN, MONO-BRANCHED AND MULTI-BRANCHED PARAFFINS

FIELD OF THE INVENTION

The invention relates to a chromatographic separation process for producing three effluents which are respectively rich in straight chain paraffins, in mono-branched paraffins, and in di-branched and tri-branched paraffins possibly with naphthenic and/or aromatic compounds, from C5–C8 cuts or intermediate cuts (C5–C7, C6–C8, C7–C8, C6–C7, C7 or C8), comprising paraffinic and possibly naphthenic and/or aromatic hydrocarbons and in some cases olefinic hydrocarbons.

The separation process of the invention uses a separation zone operating by adsorption. The process is suitable for liquid or gas phase operation. The separation zone of the invention contains at least one adsorbent which operates by preferentially adsorbing straight chain paraffins, mono-branched paraffins to a lesser extent and finally, multi-branched paraffins and naphthenic and/or aromatic compounds which may be present, to a minor extent. The separation process of the invention is particularly suitable when coupled with the hydro-isomerization process described in the patent application entitled "High octane number gasolines and their production using a process associating hydro-isomerization and separation", filed Nov. 25, 1997 by the present Assignee, since it enables straight chain and mono-branched paraffins to be selectively recycled, necessary for paraffins containing at least 7 carbon atoms.

When the feed for the process comprises a C5 cut, isopentane from that cut can either be separated using the process of the invention with the mono-branched paraffins or the multi-branched paraffins depending on the implementation selected, or it can be extracted from the streams traversing the process using at least one deisopentanizer located upstream and/or downstream of the separation unit. In the latter case, the isopentane can act as an eluent in the chromatographic separation step.

BACKGROUND OF THE INVENTION

Increasing environmental constraints have resulted in the removal of lead compounds from gasoline, effectively in the United States and Japan and becoming general in Europe. Aromatic compounds, the main constituents of reformed gasolines, and isoparaffins produced by aliphatic alkylation or isomerization of light gasoline, initially compensated for the octane number loss resulting from removing lead from gasoline. Subsequently, oxygen-containing compounds such as methyl tert.-butyl ether (MTBE) or ethyl tert.-butyl ether (ETBE) were introduced into the fuels. More recently, the known toxicity of compounds such as aromatic compounds, in particular benzene, olefins and sulphur-containing compounds, as well as the desire to reduce the vapour pressure of the gasolines, led the United States to produce reformulated gasolines. As an example, the maximum amounts of olefins, aromatic compounds and benzene in gasoline distributed in California in 1996 were respectively 6% by volume, 25% by volume, and 1% by volume. Regulations are less severe in Europe, but nevertheless there is a distinct tendency, to reduce to a similar level the maximum benzene, aromatic compound and olefin amounts in gasoline which is produced and sold.

Gasoline pools contain a plurality of components. The major components are reformed gasoline, which normally comprises between 60% and 80% by volume of aromatic compounds, and catalytic cracking (FCC) gasoline which typically contains 35% by volume of aromatic compounds but provides the majority of olefinic and sulphur-containing compounds present in the gasoline. The other components can be alkylates, with neither aromatic compounds nor olefinic compounds, light gasolines which may or may not be isomerized, which contain no unsaturated compounds, oxygen-containing compounds such as MTBE, and butanes. Since the aromatic compound content is not reduced below 30% or 40% by volume, the contribution of reformates to gasoline pools will remain high, typically 40% by volume. Increased severity as regards the maximum admissible amount of aromatic compounds to 20–25% by volume will result in a reduction in the use of reforming, and as a result the need to upgrade C7–C10 straight run cuts by routes other than reforming. Upgrading by hydro-isomerization is one possible route, as described in the patent application entitled "High octane number gasolines, and their production using a process associating hydro-isomerization and separation", filed Nov. 25, 1997 by the present Assignee. The hydro-isomerization process leads to the formation of multi-branched compounds from low octane number compounds. It can only be used to recycle straight chain and mono-branched C7–C10 paraffins, since the hydro-isomerization reaction is equilibrated and low octane number paraffins cannot be sent to the gasoline pool. Further, different hydro-isomerization conditions must be employed for those isomeric paraffins to avoid cracking the most highly branched paraffins. These two points justify research for separation processes which can produce three distinct effluents, respectively an effluent which is rich in straight chain paraffins, an effluent which is rich in mono-branched paraffins and an effluent which is rich in multi-branched paraffins and possibly in naphthenic and/or aromatic compounds.

The use of adsorption separation processes to separate straight chain, mono-branched and multi-branched paraffins has already been the subject of a number of patents (for example U.S. Pat. Nos. 4,717,784, 4,956,521 and 5,233,120, BE-A-891 522, French patent FR-A-2 688 213, U.S. Pat. Nos. 5,055,633, 4,367,364 and 4,517,402). However, those patents only concern a light C5–C6 fraction, and, further, only concern the separation of those distillation cuts into two effluents, one with a low octane number and the other with a high octane number.

Thus, U.S. Pat. Nos. 4,210,771 and 4,709,116 describe separating straight chain paraffins from a C5–C6 naphtha cut using an adsorbent known as calcium 5A zeolite. Further, U.S. Pat. No. 4,367,364 describes this same separation carried out using silicalite (U.S. Pat. No. 4,061,724). Similarly, French patent application FR-A-2 496 486 describes a chromatographic type process which enables the same separation to be carried out using a type A, X, Y or ZSM-5 zeolite. The process considered enables any gaseous feed composed of more than two groups of analogous constituents to be treated and leads to the production of two effluents. That process is characterized in that during the first step, the gas mixture to be treated is injected until the adsorbent is saturated then, after stopping continuous injection of the gas mixture, a vector gas which may be nitrogen, helium or hydrogen or a mixture of one of those non adsorbable inert gases is injected in a second step with a maximum of 40% of the gas injected in the first step. That process enables an enriched fraction containing the purified adsorbed group of constituents and a fraction containing the other groups of constituents of the mixture to be successively recovered from the column outlet. Such a process is particularly suitable for fractionating a C5–C6 cut into two fractions as shown in the examples of patent application FR-A-2 496 486. In that case, the process produces two gaseous streams, the first being rich in straight chain paraffins, and the second being rich in branched paraffins (monobranched and multi-branched), the two effluents being diluted in an effluent selected from the following three non adsorbable inert gases: nitrogen, helium and hydrogen.

The separation processes described in those various patents are often coupled with a process for isomerizing straight chain paraffins since they have a low octane number.

Similarly, some patents (such as U.S. Pat. Nos. 4,717,784 and 5,055,633) describe processes for separating straight chain paraffins and mono-branched paraffins from a C5–C6 cut. Such straight chain and mono-branched paraffins constitute the low octane number pool, while multi-branched paraffins constitute the high octane number pool. Those patents underline the importance of using adsorbents such as ferrierite (U.S. Pat. Nos. 4,804,802 and 4,717,784), ZSM-5 zeolites (U.S. Pat. No. 3,702,886), ZSM-11 (U.S. Pat. No. 4,108,881), ZSM-23 (U.S. Pat. No. 4,076,842) and ZSM-35 (U.S. Pat. No. 4,016,245), and silicalite (U.S. Pat. No. 5,055,633), since such adsorbents adsorb both straight chain and mono-branched compounds from C5–C6 cuts and exclude paraffins with higher degrees of branching. When using such adsorbents, isopentane is separated from the feed and is sent to the low octane number pool with the straight chain and mono-branched paraffins, since the octane number of that compound is high. U.S. Pat. No. 5,055,633 thus underlines the importance of producing isopentane with the stream which is rich in multi-branched compounds, naphthenic compounds and/or aromatic compounds from a C5–C6 feed. The feed contains at least 10 mole % of isopentane as well as C7+ compounds in quantities of less than 10 mole %. Such a process results in a secondary stream which is rich in straight chain paraffins and mono-branched paraffins which can be sent to an isomerization reactor.

The patents cited above do not envisage fractionating C5–C6 cuts into three effluents during isomerization for two reasons: firstly, the octane number of mono-branched C5–C6 paraffins is usually judged to be sufficient for those compounds to be sent to the gasoline pool, in which case such paraffins are separated with the multi-branched paraffins. Secondly, when the straight chain paraffins and the mono-branched paraffins are recycled to the isomerization step, it is no use separating them since those compounds can be isomerized under the same operating conditions, in contrast to heavier cuts such as those used in the present invention.

U.S. Pat. No. 5,055,634 is the only patent to describe a process which could produce three streams respectively rich in straight chain paraffins, in mono-branched paraffins and in multi-branched paraffins from a light C5–C6 cut, but its main importance, as described in the process of U.S. Pat. No. 5,055,633, lies in the possibility of separating and producing isopentane with the stream which is rich in multi-branched paraffins. The feed for such a process contains at least 10 mole % of isopentane. It is centred around C5–C6 and can sometimes contain small quantities of paraffins containing seven or more carbon atoms. As a result, the process described in that patent is suitable for contents of those C7+ compounds of less than 10 mole %.

The process described in U.S. Pat. No. 5,055,634 is carried out in two units disposed in series. The feed arrives in the first unit which contains an adsorbent which can selectively retain straight chain paraffins. The effluent from that unit is then constituted by mono- and multi-branched paraffins. That "denormalized" effluent is then introduced into the second unit which is filed with an adsorbent which can preferentially retain mono-branched paraffins with the exception of isopentane, which is produced with the multi-branched paraffins. That patent indicates that the two units are regenerated using a non adsorbable gas such as hydrogen. That gas passes firstly through the second unit and desorbs mono-branched paraffins. At least a portion of that stream is then sent to the first unit and desorbs straight chain paraffins contained therein. That regeneration mixes a portion of the mono-branched paraffins with the straight chain paraffins previously separated with the exception of isopentane, which is recovered with the high octane number compounds in the production stream. In a preferred version of the process, all of the desorption streams leaving the second unit pass through the first to minimise the quantity of non adsorbable gas required to regenerate the two units. In the latter case, the process produces only two streams, the first being rich in multi-branched paraffins, naphthenic compounds, aromatic compounds and isopentane, the second being rich in straight chain and mono-branched paraffins. Such a separation can thus be carried out using a single adsorber containing two types of adsorbents as described in the example given in U.S. Pat. No. 5,055,634.

The adsorption separation techniques recommended in those different patents to upgrade C5–C6 cuts are known in the art. Thus processes for separation by adsorption can be based on PSA (pressure swing adsorption), TSA (temperature swing adsorption), chromatography (elution chromatography or simulated counter-current chromatography, for example), or they result from a combination of the above techniques. Such processes all involve bringing a liquid or gaseous mixture into contact with a fixed bed of adsorbent to eliminate certain constituents of the mixture which may be adsorbed.

Chromatography or isobaric fractionation, in the gas or liquid phase, is a highly effective separation technique because a very large number of theoretical plates is used. It can thus exploit relatively low adsorption selectivities and accomplish difficult separations. The N-ISELF® process from Elf Aquitaine (BE-A-891 522) ("Separating Paraffin Isomers Using Chromatography", chemical engineering 18, p92–95 (1981)) for separating C5–C6 n/iso-paraffins, and the ASAHI process (Seko M., Miyake J., Inada K.: Ind. Eng. Chem. Prod. Res. Develop., 1979, 18, 263) for separating para-xylene and ethylbenzene from an aromatic C8 cut, use this type of operation to separate into two streams. Such isobaric separation techniques are known in the art. A more detailed description can be found in the more general work by Yang ("Gas Separation by Adsorption Processes", Butterworth Publishers, US, 1987).

SUMMARY OF THE INVENTION

The invention provides a chromatographic separation process for producing three effluents, respectively rich in straight chain paraffins, in mono-branched paraffins and in di-branched and tri-branched paraffins and possibly in naphthenic and/or aromatic compounds, from light C5–C8 cuts or intermediate cuts, such as C5–C7, C6–C8, C7–C8, C6–C7, C7 or C8, comprising paraffinic and possibly naphthenic, aromatic and in some cases, olefinic hydrocarbons.

The separation process of the invention comprises a separation zone and is suitable for liquid or gas phase operation. Such a separation process is of particular application when it is coupled with a hydro-isomerization process as described in the patent application entitled "High octane number gasolines and their production using a process associating hydro-isomerization and separation" filed Nov. 25, 1997 by the present Assignee, French application 97/14.891. The process described necessitates recycling of both the straight chain paraffins (nCx, x=5 to 8) and mono-branched paraffins (monoC(x−1)), since the octane numbers of C7–C8 paraffins are low (see Table 1 below). This French application discloses a preferred hydroisomerization feed having at least 12 mole percent of C7+ hydrocarbons. Further, different hydro-isomerization conditions must be employed for the two types of isomers to avoid cracking the most highly branched paraffins. These two points justify research for a separation process which can produce three distinct effluents, respectively rich in straight chain paraffins nCx, in mono-branched paraffins monoC(x−1), and in multi-branched paraffins (diC(x−2) or triC(x−3)), naphthenic compounds and/or aromatic compounds.

TABLE 1

| Paraffin | nC7 | monoC6 | diC5  | triC4 | nC8 | monoC7 | diC6  | triC5   |
|----------|-----|--------|-------|-------|-----|--------|-------|---------|
| RON      | 0   | 42–52  | 80–93 | 112   | <0  | 21–27  | 55–76 | 100–109 |
| MON      | 0   | 23–39  | 84–95 | 101   | <0  | 23–39  | 56–82 | 96–100  |

In general, the process of the invention is characterized in that the feed is periodically injected into a chromatographic separation zone alternately with an adsorbable or non adsorbable eluent. The chromatographic separation zone of the invention contains at least one adsorbent which is used so that it preferentially adsorbs straight chain paraffins, mono-branched paraffins to lesser extent and finally, multi-branched paraffins and naphthenic and aromatic compounds to a minor extent. The eluant is selected so as to enable the different adsorbed compounds in the feed to be desorbed. This process can successively recover from the adsorber outlet a first fraction which is enriched in multi-branched paraffins and possibly in naphthenic and/or aromatic compounds, a second fraction which is enriched in mono-branched paraffins and finally, a last fraction which is enriched in straight chain paraffins.

DETAILED DESCRIPTION OF THE INVENTION

The feed treated in the process of the invention originates from a C5–C8 cut or any intermediate cuts (such as C5–C7, C6–C8, C6–C7, C7–C8, C7 or C8) from atmospheric distillation, from a reforming unit (light reformate) or from a conversion unit (naphtha hydrocracking, for example). In the remainder of the text, this set of possible feeds will be designated by the term "C5–C8 cuts and intermediate cuts".

In general, the feed which is treated is mainly composed of straight-chain, mono-branched and multi-branched paraffins, naphthenic compounds such as di-methylcyclopentanes, aromatic compounds such as benzene and/or toluene, and possibly olefinic compounds. The term "multi-branched paraffins" includes all paraffins with a degree of branching of two or more.

The feed can contain normal pentane, 2-methylbutane, neopentane, normal hexane, 2-methylpentane, 3-methylpentane, 2,2-dimethylbutane, 2,3-dimethylbutane, normal heptane, 2-methylhexane, 3-methylhexane, 2,2-dimethylpentane, 3,3-dimethylpentane, 2,3-dimethylpentane, 2,4-dimethylpentane, 2,2,3-trimethylbutane, normal octane, 2-methylheptane, 3-methylheptane, 4-methylheptane, 2,2-dimethylhexane, 3,3-dimethylhexane, 2,3-dimethylhexane, 3,4-dimethylhexane, 2,4-dimethylhexane, 2,5-dimethylhexane, 2,2,3-trimethylpentane, 2,3,3-trimethylpentane, and 2,3,4-trimethylpentane. When the feed originates from C5–C8 cuts or intermediate cuts (such as C5–C7, C6–C8, C6–C7, C7–C8, C7, C8) obtained after atmospheric distillation, it can also contain cyclic alkanes such as dimethylcyclopentanes, aromatic hydrocarbons (such as benzene, toluene, xylenes) and other C9+ hydrocarbons (i.e., hydrocarbons containing at least 9 carbon atoms) in small quantities. The C5–C8 cuts and intermediate cuts from reformates can also contain olefinic hydrocarbons, in particular when the reforming units are operated at low pressure.

The amount of paraffins (P) essentially depends on the origin of the feed, i.e., on its paraffinic or naphthenic and aromatic character, sometimes measured using the parameter N+A (the sum of the amount of naphthenes (N) and the amount of aromatic compounds (A)), also its initial point, i.e., the amount of C5 and C6 in the feed. In hydrocracked naphthas, which are rich in naphthenic compounds, or light reformates, which are rich in aromatic compounds, the amount of paraffins in the feed will generally be low, of the order of 30% by weight. In straight run C5–C8 cuts or intermediate cuts, the amount of paraffins varies between 30% and 80% by weight, with an average value of 55–60% by weight.

The feed which is rich in paraffins containing between 5 and 8 carbon atoms generally has a low octane number and the process of the invention consists of fractionation into three distinct effluents with increasing motor and research octane numbers, respectively rich in straight chain paraffins, in mono-branched paraffins and in di-branched, tri-branched and possibly in naphthenic and/or aromatic compounds.

Fractionation takes place in a separation zone containing one or more adsorbents, using an adsorbable or non adsorbable eluent. The process of the invention is suitable for liquid or gas phase operation. Further, in general a plurality of separation units (for example two to fifteen) are used in parallel and alternately to lead to a process which operates continuously, even though a chromatographic process such as that of the invention is by nature discontinuous.

The process of the invention is characterized in that the feed is periodically injected into a separation zone (or adsorber) alternately with an adsorbable or non adsorbable eluent. The separation zone of the invention contains at least one adsorbent which is used such that it preferentially adsorbs straight chain paraffins, to a lesser extent mono-branched paraffins, and finally minor amounts of multi-branched paraffins and naphthenic and aromatic compounds. As a result, in the adsorber, during feed injection, adsorption fronts of these different constituents are created. An adsorbable or non adsorbable eluant is then injected into the adsorber. The eluent is selected so as to desorb the different compounds adsorbed by the feed, which then traverse the adsorber along distinct desorption fronts. This process enables a first fraction which is enriched in multi-branched paraffins, and possibly naphthenic and/or aromatic compounds, a second fraction which is enriched in mono-branched paraffins and finally a last fraction which is enriched in straight chain paraffins, to be successively recovered from the adsorber outlet.

When the feed comprises olefinic compounds, their fractionation in the chromatographic separation step occurs depending on their degree of branching, similarly to paraffinic compounds.

The eluant used in the process of the invention can be non adsorbable, in which case the adsorbent is regenerated by reducing the concentrations of the adsorbed species. In that case, hydrogen, nitrogen, helium or any compound which is geometrically excluded from the pores of the adsorbent can be used.

The eluant can also comprise at least one adsorbable compound, i.e., capable of adsorbing on at least one of the adsorbents, used. In that case, regeneration of the adsorbent is at least partially ensured by displacing the adsorbed species. Examples of adsorbable species are propane, butane, pentane, isopentane, etc.

It may be advantageous in the process of the invention to use a compound originating from the feed as the eluant. When the feed contains a C5 cut, the isopentane from that cut can either be separated by the process of the invention in the effluent containing mono-branched paraffins or in that containing the multi-branched paraffins, depending on the implementation selected, or it can be extracted from the streams traversing the process using at least one deisopentanizer located upstream and/or downstream of the separation unit. In the latter case, the separated isopentane can act as the eluant for chromatographic separation.

More generally, it may be of interest to remove one or more light fractions from the feed upstream of the adsorber or one or more light fractions from the streams obtained at the adsorber outlet enriched either in straight chain paraffins, or in mono-branched paraffins. These different light fractions can thus act as an adsorbable eluant to carry out separation. As an example, a depentanizer can be placed upstream of the adsorber when the feed contain a C5 cut. The pentane and isopentane-rich mixture thus recovered can then act as the eluant for chromatographic separation.

The chromatographic separation zone is filled with a natural or synthetic adsorbent which can separate straight chain paraffins, mono-branched paraffins and multi-branched paraffins, naphthenic and/or aromatic compounds on the basis of differences in the geometrical, diffusional or thermodynamic properties of the adsorbates for the adsorbents under consideration. A large number of adsorbent materials exist which can carry out this type of separation. Among them are carbon molecular sieves, activated clay, silica gel, and activated alumina, and crystalline molecular sieves. These latter have a uniform pore size and for this reason are particularly suitable for separation. Such molecular sieves include the different forms of silicoaluminophosphates and aluminophosphates described in U.S. Pat. Nos. 4,444,871, 4,310,440 and 4,567,027 as well as zeolitic molecular sieves. These, in their calcined form, can be represented by the chemical formula:

$$M_{2/n}O: Al_2O_3: xSiO_2: yH_2O$$

where M is a cation, x is in the range 2 to infinity, y is in the range 2 to 10 and n is the valency of the cation.

Microporous molecular sieves with a pore diameter which is slightly over 5 Å (1 Å=$10^{-10}$ m) are preferred for use in the process of the invention. The term "pore diameter" is a conventional term in the art. It is a functional measurement used to define pore size in terms of the size of molecule which can enter the pore. It does not define the actual dimension of the pore as that is often difficult to determine since the pore is usually irregular in shape (i.e., non circular). D. W. Breck discusses the effective pore diameter in his book entitled "Zeolite Molecular Sieves", John Wiley and Sons, New York, 1974), pages 633 to 641. Among molecular sieves which are preferred for use in the process of the invention are sieves with elliptical pore cross sections with dimensions in the range 5.0 Å to 5.5 Å along the minor axis and about 5.5 to 6.0 Å along the major axis. An adsorbent with these characteristics, and thus particularly suitable for the present invention, is silicalite. The term "silicalite" includes here both silicopolymorphs described in U.S. Pat. No. 4,061,724 and F silicalite described in U.S. Pat. No. 4,073,865. Other adsorbents with the same characteristics and thus which are particularly suitable for our application are ZSM-5, ZSM-11, ZSM-23 (U.S. Pat. No. 4,076,842), ZSM-35 (U.S. Pat. No. 4,016,245), ZSM-48 and numerous other analogous crystalline alumino-silicates. ZSM-5 and ZSM-11 are described in U.S. Pat. Nos. 3,702,886, RE 29,948 and 3,709,979. The amount of silica in these adsorbents can vary. Adsorbents which are the most suitable for this type of separation are those with high silica contents. The Si/Al molar ratio should preferably be at least 10 and more preferably over 100. A further type of adsorbent which is particularly suitable for our application contains elliptical cross section pores with dimensions in the range 4.5 Å to 5.5 Å. This type of adsorbent has been described in U.S. Pat. No. 4,717,748, for example, as being a tectosilicate with a pore size intermediate between that of pores of a calcium 5A sieve and the pores of ZSM-5. Preferred adsorbents include ZSM-5, ZSM-11 and ZSM-23, also ferrierite (described in U.S. Pat. Nos. 4,016,425 and 4,251,499).

These different adsorbents have pore sizes such that each of the isomers of C5–C8 or intermediate cuts can be adsorbed. The diffusion kinetics for these isomers is, however, sufficiently different to be usefully exploited. Under certain operating conditions, these molecular sieves can carry out separation into three effluents as described in the present invention. Details of the adsorption of straight chain, mono-branched, multi-branched paraffins, naphthenic and aromatic compounds on each of these sieves are known to the skilled person and this process thus does not warrant a more detailed description here.

It may also be of interest to the present invention to mix type 5A zeolites, such as those described in U.S. Pat. No. 2,882,243, with the absorbents cited above. In the majority of their cationic exchanged forms, in particular in the calcium form, such zeolites have a pore diameter of the order of 5 Å and have large capacities for adsorbing straight chain paraffins. Mixed with the zeolites cited above, they may accentuate separation of the elution fronts and thus produce higher purity of each of the enriched streams obtained.

The operating conditions for the separation unit depend on the adsorbent or adsorbents considered, and on the degree of purity desired for each stream. They are a temperature in the range 50° C. to 450° C. and a pressure of 0.01 to 7 MPa. More precisely, if separation is carried out in the liquid phase, the separation conditions are: a temperature of 50° C. to 250° C. and a pressure of 0.1 to 7 MPa. If said separation is carried out in the gas phase, these conditions are: a temperature of 150° C. to 450° C. and a pressure of 0.01 to 7 MPa. The duration of the periodic injections of mixture to be treated is in the range 1 to 200 seconds. The duration of each cycle is in the range 10 to 2000 seconds and the injection/cycle duration ratio is less than 0.5.

The entire disclosure of all applications, patents and publications, cited above and below, and of corresponding French application 98/01390, filed Feb. 4, 1998, are hereby incorporated by reference.

EXAMPLES

The following examples illustrate the invention without limiting it in any way.

Example 1

The example below concerns chromatographic separation carried out by gas phase adsorption using a straight run C5–C8 cut comprising paraffinic, naphthenic and aromatic hydrocarbons.

The fresh feed for the process had the composition indicated in Table 2 and as a result it had a research octane number of 65 and a motor octane number of 63.5.

Fresh feed was sent to a deisopentanizer at a rate of 273.5 kg/h. The light fraction recovered overhead from this deisopentanizer n°1 had the composition shown in Table 3, a research octane number of 92.4 and a flow rate of 28.5 kg/h. This fraction was then used as an eluant in the separation unit.

TABLE 2

| Components | Weight, % |
|---|---|
| iC4 | 0.02 |
| nC4 | 0.91 |
| nC5 | 15.23 |
| iC5 | 9.50 |
| cyclopentane | 0.73 |
| nC6 | 15.80 |
| mono-branched C6 | 12.61 |
| di-branched C6 | 5.30 |
| cyclohexane | 2.34 |
| methylcyclopentane | 3.27 |
| nC7 | 7.45 |
| mono-branched C7 | 3.95 |
| di-branched C7 | 1.06 |
| tri-branched C7 | 1.20 |
| dimethylcyclo C5 | 4.58 |
| methylcyclo C6 | 3.79 |
| nC8 | 1.12 |
| mono-branched C8 | 0.93 |
| di-branched C8 | 0.77 |
| tri-branched C8 | 0.28 |
| trimethylcyclo C5 | 4.03 |
| ethylbenzene | 0.99 |
| toluene | 3.73 |
| benzene | 0.41 |

TABLE 3

| Component | Weight, % |
|---|---|
| nC4 | 7 |
| iC4 | 0.15 |
| iC5 | 92.85 |

The deisopentanized feed (flow rate 245 kg/h), first reheated and vaporized at 250° C. and at a pressure of 1.0 MPa, arrived in the separation unit. This unit comprised 9 adsorbers which were cylinders with an internal diameter of 0.3 m and a height of 4 m, each containing 226 kg of silicalite, formed into 1.2 mm diameter beads. The feed and eluant were supplied to the separation unit at a controlled flow rate and the effluents were recovered under controlled pressure. Each separation unit underwent the following cyclic steps.

1. Injection of Deisopentanized Feed

The deisopentanized feed (245.05 kg/h) penetrated into the bed which contained eluant gas. Because of their different diffusion kinetics and thermo-dynamic adsorption properties in the adsorbent, the compounds were retained in distinct adsorption fronts. The straight chain paraffins were retained to the greatest extent, while the multi-branched paraffins, naphthenic and aromatic compounds were only retained to a very slight extent under the operating conditions.

2. Injection of Eluant

The isopentane was then sent as a counter-current to the first step with the same flow rate as the feed. The isopentane selectively desorbed the different adsorbed compounds. Its introduction led to the formation of a number of elution streams in the separation unit.

Thus at the outlet from the adsorber, three streams were recovered which were respectively enriched in dibranched paraffins, naphthenic compounds and aromatic compounds, in mono-branched paraffins and in straight chain paraffins.

The operation described above was that of one of the adsorbers. The nine adsorbers which formed the separation unit operated in the same way but offset from each other so as to result in continuous production of the three effluents.

The feed was injected for 50 seconds, and the eluant was injected for 450 seconds.

The stream enriched in multi-branched paraffins, in naphthenic compounds and in aromatic compounds was collected at the adsorber outlet for 166 seconds. The research octane number of this fraction was 91.9. This stream contained 89% of isopentane, 0.26% of straight chain paraffins and 0.97% of mono-branched paraffins.

The stream enriched in mono-branched paraffins was then collected from the adsorber outlet for 99 seconds. The research octane number of this fraction was 89.7. This stream contained 90% of isopentane, 1.48% of straight chain paraffins and 1.78% of dibranched paraffins, naphthenic compounds and aromatic compounds.

Finally, the stream enriched in straight chain paraffins was collected from the adsorber outlet for 235 seconds. The research octane number of this fraction was 86.8. This stream contained 91% of isopentane, 0.68% of monobranched paraffins and 0.08% of dibranched paraffins, naphthenic compounds and aromatic compounds.

Overall, the process of the invention led to the production of three effluents, respectively rich in straight chain paraffins, in mono-branched paraffins and in multi-branched paraffins, naphthenic compounds and/or aromatic compounds, from a straight run C5–C8 cut comprising paraffinic, naphthenic and/or aromatic hydrocarbons.

It should be remembered that within the context of the invention "High octane number gasolines and their production using a process associating hydro-isomerization and separation" which formed the subject matter of a patent application filed in France Nov. 25, 1997 by the present Assignee, the three enriched streams which leave the separation step can be sent to hydro-isomerization units for the two streams with the lowest octane number, and to the "gasoline pool" for the high octane number stream. The streams leaving the hydro-isomerization sections can then be recycled to the process described above. It may also be of interest, for example with the aim of limiting the volume of the hydro-isomerization sections, to deisopentanize the stream enriched in mono-branched paraffins and/or the stream enriched in straight chain paraffins. The stream enriched in multi-branched paraffins and possibly in naphthenic and/or aromatic compounds can also be sent to a deisopentanizer.

The following example describes the case where the three streams from the chromatographic separation step are treated with deisopentanizers.

Example 2

Example 1 was repeated, but the three enriched streams obtained were treated as described below.

These three streams were respectively sent to three distinct deisopentanizers (respectively deisopentanizer n°2 for the stream enriched in multi-branched paraffins, deisopentanizer n°3 for the stream enriched in mono-branched paraffins and deisopentanizer n°4 for the stream enriched in straight chain paraffins) to extract isopentane from these three streams and recycle it as an eluant gas to the separation unit. The compositions of the three streams from the three deisopentanizers, respectively rich in multi-branched paraffins, naphthenic compounds and aromatic compounds, in mono-branched paraffins and in straight chain paraffins, are shown in Table 4.

The process illustrated in this example requires recycling of a certain quantity of the isopentane between deisopentanizers n°2, n°3 and n°4 and the 9 chromatographic separation units, in a closed loop. The flow rate of this eluant gas can be adjusted as a function of the specifications of the separation units. A portion of this eluant gas circulating in a closed loop can be removed. This portion corresponds to the quantity of light fraction removed by fresh feed deisopentanizer n°1.

What is claimed is:

1. A process for separating isomers from a cut of C5–C8, C5–C7, C6–C8, C7–C8, C6–C7, C7 or C8 compounds, comprising paraffinic hydrocarbons, and optionally, naphthenic and/or aromatic hydrocarbons, said process comprising passing (A) a feed comprising said cut and (B) an eluant alternately and periodically into a chromatographic separation zone containing only one adsorbent, so as to obtain three separate effluents, respectively an effluent rich in straight chain paraffins, an effluent rich in mono-branched paraffins and an effluent rich in multi-branched paraffins and optionally in naphthenic and/or aromatic compounds, said eluant (B) comprising a non-adsorbable compound which is geometrically excluded from the pores of the adsorbent, or an adsorbable compound capable of adsorbing on said adsorbent and being at least one of propane, butane, pentane, isopentane, and a fraction separated from the cut subjected to the separation process or from the effluent from the separation process.

2. A process according to claim 1, wherein the feed comprises a C5 cut, and isopentane from this cut is separated with the effluent rich in mono-branched paraffins.

3. A process according to claim 1, wherein the feed comprises a C5 cut and isopentane contained in this cut is extracted from the effluent which is rich in mono-branched paraffins leaving the process.

4. A process according to claim 1, wherein the feed comprises a C5 cut, isopentane contained in this cut is extracted from the feed upstream of the chromatographic separation zone or from at least one of the effluents leaving the process, and in that the isopentane thus extracted acts as an eluant for the chromatographic separation zone.

5. A process according to claim 3, wherein isopentane is extracted from the effluent which is rich in mono-branched

TABLE 4

| Composition of stream enriched in straight chain paraffins after passing through deisopentanizer n ° 2 | (wt %) | Composition of stream enriched in mono-branched paraffins after passing through deisopentanizer n ° 3 | (wt %) | Composition of stream enriched in multi-branched paraffins after passing through deisopentanizer n ° 4 | (wt %) |
| --- | --- | --- | --- | --- | --- |
| nC5 | 35 | isopentane | 0.5 | multi-branched C6 | 15.9 |
| nC6 | 36 | mono-branched C6 | 48 | di-branched C7 | 7.6 |
| nC7 | 17 | mono-branched C7 | 15 | multi-branched C8 | 3.1 |
| nC8 | 2.5 | mono-branched C8 | 3.5 | aromatic and naphthenic compounds | 59.1 |
| mono-branched compounds | 8.7 | straight chain compounds | 15 | mono-branched compounds | 11.7 |
| multi-branched compounds | 0.8 | multi-branched compounds | 18 | straight chain compounds | 2.6 |
| RON | 36.5 | | 67.3 | | 92.4 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

paraffins leaving the process and acts as an eluant in the chromatographic separation zone.

6. A process according to claim 1, wherein said at least one adsorbent comprises a member selected from the group consisting of silicalite, ZSM-5 zeolite, ZSM-11 zeolite, ZSM-23 zeolite and ferrierite.

7. A process according to claim 6, characterized in that said adsorbent also comprises a 5A zeolite.

8. A process according to claim 1, wherein the chromatographic separation is carried out in the liquid phase.

9. A process according to claim 1, wherein the chromatographic separation is carried out in the gas phase.

10. A process according to claim 1, wherein the feed originates from atmospheric distillation.

11. A process according to claim 1, wherein the feed originates from a reforming unit.

12. A process according to claim 1, wherein the feed originates from a conversion unit.

13. A process according to claim 1, characterized in that the effluents which are respectively rich in straight chain paraffins and in mono-branched paraffins are sent to at least one hydro-isomerization reactor and the effluent which is rich in multi-branched paraffins and optionally in naphthenic and/or aromatic compounds is sent to the gasoline pool.

14. A process according to claim 12, wherein the feed is obtained from a prior step comprising hydrocracking naphtha.

15. A process according to claim 1, wherein said cut of C5–C8 compounds or intermediate C5–C7, C6–C8, C7–C8, C6–C7, C7 or C8 compounds, contains more than 12 mole % of C7+ hydrocarbons.

16. A process in accordance with claim 1, wherein the eluant (B) is isopentane.

17. A process according to claim 1, wherein said only one adsorbent is silicalite.

18. A process according to claim 1, wherein said eluant is a non-adsorbable compound other than hydrogen.

19. A process according to claim 1, wherein said eluant is a non-adsorbable compound comprising at least one of nitrogen and helium.

20. A process according to claim 1, characterized in that the feed comprises a C5 cut and isopentane contained in this cut is extracted from the feed upstream of the chromatographic separation zone.

21. A process according to claim 1, characterized in that the feed comprises a C5 cut and isopentane contained in this cut is extracted from at least one of the effluents leaving the process.

22. A process according to claim 1, characterized in that the feed comprises a C5 cut, isopentane contained in this cut is extracted from the feed upstream of the chromatographic separation zone or from at least one of the effluents leaving the process, and in that the isopentane thus extracted acts as an eluant for the chromatographic separation zone.

23. A process according to claim 1, characterized in that isopentane is extracted from the effluent which is rich in mono-branched paraffins leaving the process and acts as an eluant in the chromatographic separation zone.

24. A process according to claim 12, wherein the feed is a naphtha obtained from a hydrocracking process.

25. A process according to claim 1, wherein said chromatographic separation zone comprises solids and fluids, said solids consisting essentially of said one adsorbent.

26. A process according to claim 1, wherein said chromatographic separation zone is fixed.

27. A process according to claim 1, wherein said eluant is passed into the chromatographic zone in a direction co-current to the direction of the feed into said zone.

* * * * *